United States Patent
Fondin et al.

(10) Patent No.: US 10,682,303 B2
(45) Date of Patent: Jun. 16, 2020

(54) COSMETIC COMPOSITION INCLUDING A MINERAL WAX, A FATTY ACID, A MINERAL OIL, A SURFACTANT, A FATTY ACID AND/OR FATTY ALCOHOL ESTER, AND A FIXING POLYMER

(71) Applicant: L'OREAL, Paris (FR)

(72) Inventors: Thomas Fondin, Taverny (FR); Franck Clement, Sainte Genevieve des Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/898,974

(22) PCT Filed: Jun. 17, 2014

(86) PCT No.: PCT/EP2014/062634
§ 371 (c)(1),
(2) Date: Dec. 16, 2015

(87) PCT Pub. No.: WO2014/202559
PCT Pub. Date: Dec. 24, 2014

(65) Prior Publication Data
US 2016/0113857 A1    Apr. 28, 2016

(30) Foreign Application Priority Data

Jun. 17, 2013  (FR) .................................... 13 55636
Jun. 17, 2013  (FR) .................................... 13 55637
Jun. 17, 2013  (FR) .................................... 13 55638

(51) Int. Cl.
| | |
|---|---|
| A61K 8/81 | (2006.01) |
| A61K 8/31 | (2006.01) |
| A61K 8/36 | (2006.01) |
| A61K 8/39 | (2006.01) |
| A61Q 5/06 | (2006.01) |
| A61K 8/92 | (2006.01) |
| A61K 8/86 | (2006.01) |
| A61K 8/34 | (2006.01) |
| A61K 8/37 | (2006.01) |

(52) U.S. Cl.
CPC .............. *A61K 8/8182* (2013.01); *A61K 8/31* (2013.01); *A61K 8/342* (2013.01); *A61K 8/361* (2013.01); *A61K 8/37* (2013.01); *A61K 8/39* (2013.01); *A61K 8/86* (2013.01); *A61K 8/92* (2013.01); *A61Q 5/06* (2013.01)

(58) Field of Classification Search
CPC ........ A61K 8/37; A61K 2800/88; A61K 8/31; A61K 8/342; A61K 8/46; A61K 2800/31; A61K 2800/882; A61K 8/361; A61K 8/375; A61K 8/415; A61K 8/42; A61K 2800/612; A61K 2800/651; A61K 8/0279; A61K 8/25; A61K 8/39; A61K 8/675; A61K 8/8182; A61K 8/86; A61K 8/92; A61K 8/922; A61Q 5/10; A61Q 5/04; A61Q 5/06; A45D 1/04; A45D 7/02
See application file for complete search history.

(56) References Cited

U.S. PATENT DOCUMENTS

| | | |
|---|---|---|
| 2,047,398 A | 7/1936 | Voss et al. |
| 2,723,248 A | 11/1955 | Wright |
| 3,579,629 A | 5/1971 | Pasero et al. |
| 3,589,978 A | 6/1971 | Kamal et al. |
| 3,716,633 A | 2/1973 | Viout et al. |
| 3,810,977 A | 5/1974 | Levine et al. |
| 3,836,537 A | 9/1974 | Boerwinkle et al. |
| 3,910,862 A | 10/1975 | Barabas et al. |
| 3,925,542 A | 12/1975 | Viout et al. |
| 3,946,749 A | 3/1976 | Papantoniou |
| 3,966,403 A | 6/1976 | Papantoniou et al. |
| 3,966,404 A | 6/1976 | Papantoniou et al. |
| 3,990,459 A | 11/1976 | Papantoniou |
| 4,031,307 A | 6/1977 | DeMartino et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,165,367 A | 8/1979 | Chakrabarti |
| 4,223,009 A | 9/1980 | Chakrabarti |
| 4,282,203 A | 8/1981 | Jacquet et al. |
| 4,289,752 A | 9/1981 | Mahieu et al. |

(Continued)

FOREIGN PATENT DOCUMENTS

| | | |
|---|---|---|
| DE | 2330956 A1 | 1/1974 |
| DE | 102007052391 A1 | 5/2009 |
| EP | 0080976 A1 | 6/1983 |
| FR | 1222944 A | 6/1960 |
| FR | 1400366 A | 5/1965 |
| FR | 1564110 A | 3/1968 |
| FR | 1580545 A | 9/1969 |
| FR | 2077143 A | 10/1971 |
| FR | 2198719 A1 | 4/1974 |
| FR | 2265781 A1 | 10/1975 |
| FR | 2265782 A1 | 10/1975 |
| FR | 2350384 A1 | 12/1977 |
| FR | 2357241 A2 | 2/1978 |

(Continued)

OTHER PUBLICATIONS

International Search Report for PCT/EP2014/062634, dated Nov. 18, 2014.

(Continued)

*Primary Examiner* — Audrea B Coniglio
(74) *Attorney, Agent, or Firm* — The Marbury Law Group, PLLC

(57) ABSTRACT

The present invention relates to a cosmetic composition comprising (i) at least one mineral wax in a content ranging from 12% to 40% by weight relative to the total weight of the composition, (ii) at least one fatty acid, (iii) at least one mineral oil, (iv) at least one surfactant, (v) at least one ester of fatty acid and/or of fatty alcohol and (vi) at least one fixing polymer.

13 Claims, No Drawings

(56) References Cited

U.S. PATENT DOCUMENTS

2005/0163738 A1* 7/2005 Loifenfeld ............... A61K 8/31
424/70.1
2010/0209376 A1* 8/2010 Richters .................. A61K 8/25
424/70.12

FOREIGN PATENT DOCUMENTS

| | | |
|---|---|---|
| FR | 2393573 A1 | 1/1979 |
| FR | 2439798 A1 | 5/1980 |
| GB | 839805 A | 6/1960 |
| GB | 922457 A | 4/1963 |
| GB | 1021400 A | 3/1966 |
| GB | 1408388 A | 10/1975 |
| GB | 1572626 A | 7/1980 |
| LU | 75370 A1 | 2/1978 |
| LU | 75371 A1 | 2/1978 |
| WO | 2011076566 A1 | 6/2011 |

OTHER PUBLICATIONS

Porter, M.R., "Handbook of Surfactants," published by Blackie & Son (Glasgow and London), 1991, pp. 116-178.
MINTEL: "Thousle Whip 04 Cream-Wax," XP002720285, Aug. 2011.
MINTEL: "5 Design Cream," XP002720286, Oct. 2012.
MINTEL: "Elastic Hair Styling Wax," XP002720287, Sep. 2010.
MINTEL: "Wax," XP002720288, Jun. 2011.
MINTEL: "Clay Strong Hair Wax," XP002720527, Sep. 2012.
First Chinese Office Action for counterpart CN Application No. 201480034518.5, dated Apr. 7, 2017.

* cited by examiner

COSMETIC COMPOSITION INCLUDING A MINERAL WAX, A FATTY ACID, A MINERAL OIL, A SURFACTANT, A FATTY ACID AND/OR FATTY ALCOHOL ESTER, AND A FIXING POLYMER

CROSS REFERENCE TO RELATED APPLICATIONS

This is a national stage application of PCT/EP2014/062634, filed internationally on Jun. 17, 2014, which claims priority to French Application Nos. 1355636, 1355637 and 1355638, all of which were filed on Jun. 17, 2013, all of which are incorporated herein by reference in their entireties.

The present invention relates to a cosmetic composition comprising at least one mineral wax, at least one fatty acid, at least one mineral oil, at least one surfactant, at least one ester of fatty acid and/or of fatty alcohol and at least one fixing polymer, and also to the use of such a composition for treating the hair, especially for treating keratin fibers and in particular for form retention/shaping of the hair.

Styling products with a wax effect are mainly in the form of more or less viscous pastes which are applied to the hair with the hands.

However, styling waxes are often sticky and greasy. Moreover, the style obtained is difficult to rework and has a sticky finish.

There is thus a real need for a cosmetic composition which has good styling and cosmetic properties, and which enables the drawbacks mentioned above to be remedied.

The Applicant discovered that, by combining at least one mineral wax in a particular content, at least one fatty acid, at least one mineral oil, at least one surfactant and at least one ester of fatty acid and/or of fatty alcohol, it was possible to obtain styling waxes with improved use qualities and improved styling performance.

A subject of the present invention is therefore a cosmetic composition comprising (i) at least one mineral wax in a content ranging from 12% to 40% by weight relative to the total weight of the composition, (ii) at least one fatty acid, (iii) at least one mineral oil, (iv) at least one surfactant, (v) at least one ester of fatty acid and/or of fatty alcohol and at least one fixing polymer.

The cosmetic composition is preferably a composition for styling and/or conditioning keratin fibers, especially for styling keratin fibers, in particular human keratin fibres such as the hair.

The invention also relates to a process for the cosmetic treatment of keratin fibers, especially for form retention and/or shaping of keratin fibers using the cosmetic composition as defined above.

Another subject of the invention is the use of a composition as defined previously, for treating the hair, especially for treating keratin fibers and in particular for form retention and/or shaping of the hair The composition obtained is easy to spread out on the hands and then on the hair. Moreover, the hairstyle is quickly shaped. The hair is not very sticky and a style with a natural finish is obtained. The hold of the style is improved, and restyling the hair is made easier.

Other subjects, characteristics, aspects and advantages of the invention will emerge even more clearly on reading the description and the examples that follow.

In that which follows, the expression "at least one" is equivalent to the expression "one or more".

The composition according to the invention comprises at least one mineral wax.

The waxes under consideration in the context of the present invention are generally lipophilic compounds that are solid and deformable or non-deformable at ambient temperature (25° C.), with a solid/liquid reversible change of state, having a melting point of greater than or equal to 30° C., which may range up to 200° C. and in particular up to 120° C.

By bringing one or more wax(es), in accordance with the invention, to the liquid state (melting), it is possible to render it (them) miscible with one or more oils and to form a macroscopically homogeneous wax(es)+oil(s) mixture, but if the temperature of said mixture is returned to ambient temperature, recrystallization of the wax(es) from the oil(s) of the mixture is obtained.

Within the context of the invention, the melting point corresponds to the temperature of the most endothermic peak observed in thermal analysis (DSC) as described in the standard ISO 11357-3; 1999. The melting point of the wax may be measured using a differential scanning calorimeter (DSC), for example the calorimeter sold under the name MDSC 2920 by the company TA Instruments.

The measuring protocol is as follows:

A sample of 5 mg of wax placed in a crucible is subjected to a first temperature rise ranging from −20° C. to 100° C., at a heating rate of 10° C./minute, then is cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in a composition according to the invention are chosen from waxes, that are preferably solid at ambient temperature, of mineral origin.

Within the context of the present invention, the term "mineral wax" is intended to mean a wax derived from petroleum, such as paraffin wax, ozokerite, ceresin or microcrystalline waxes, such as, for example, microcrystalline waxes with a melting point of greater than 85° C. such as the HI-MIC® 1070, 1080, 1090 and 3080 products sold by the company Nippon Seiro.

According to one particular embodiment, the wax used in a composition in accordance with the invention has a melting point of greater than 35° C., better still greater than 40° C., or even greater than 45° C. or greater than 55° C.

According to one particular embodiment of the invention, the composition comprises a microcrystalline wax and/or ozokerite.

The content of mineral wax(es) ranges from 12% to 40%, preferably from 12% to 35% and better still from 12% to 30% by weight relative to the total weight of the composition.

The composition according to the invention also comprises at least one fatty acid.

The fatty acid may be liquid or non-liquid.

The term "liquid fatty acid" is intended to mean a fatty acid which is liquid at normal temperature (25° C.) and at atmospheric pressure (760 mmHg; i.e. $1.013 \times 10^5$ Pa).

Preferably, the fatty acids of the invention comprise from 8 to 30 carbon atoms.

The fatty acids of the invention may be saturated or unsaturated.

The saturated liquid fatty acids are preferably branched. They may optionally comprise in their structure at least one aromatic or non-aromatic ring. They are preferably acyclic.

Mention may be made more particularly of isostearic acid.

The unsaturated fatty acids contain in their structure at least one double or triple bond, and preferably one or more double bonds. When several double bonds are present, there are preferably 2 or 3 of them, and they may be conjugated or unconjugated.

These unsaturated fatty acids may be linear or branched.

They may optionally comprise in their structure at least one aromatic or non-aromatic ring. They are preferably acyclic.

In a first variant, the fatty acids of the invention are liquid.

Mention may be made more particularly of oleic acid.

In a second variant of the invention that is particularly commended, the fatty acid is non-liquid and preferably solid.

The non-liquid fatty alcohols suitable for the implementation of the invention are chosen more particularly from saturated or unsaturated and linear or branched acids comprising from 8 to 30 carbon atoms.

As fatty acids of this type, mention will be made, for example, of stearic acid, palmitic acid, myristic acid and behenic acid and mixtures thereof.

The fatty acid(s) may be present in the composition in a content ranging from 0.1% to 10%, preferably from 0.5% to 7% and better still from 1% to 5% by weight relative to the total weight of the composition.

The composition according to the present invention also comprises one or more mineral oils.

The term "oil" is intended to mean any nonionic lipophilic compound that is water-insoluble and liquid at ambient temperature (25° C.) and at atmospheric pressure. Within the context of the present invention, the term "water-insoluble" is intended to mean a compound of which the solubility at spontaneous pH in water at 25° C. and at atmospheric pressure is less than 1% and preferably less than 0.5%. Oils preferably have a melting point of less than 5° C. and a viscosity of less than 500 cPs at 25° C. at a shear rate of 1 $s^{-1}$.

The term "mineral oils" is intended to mean hydrocarbons in the form of linear or branched, saturated or unsaturated oils, of mineral or synthetic origin, and which may be hydrogenated.

The mineral oils used in the present invention are chosen from the mineral oils as defined above, usually used in the cosmetics field.

As examples of mineral oils that may be used in the present invention, mention may be made of:

mixtures of hydrocarbon-based oils derived from petroleum (INCI name: Mineral Oil),
volatile or non-volatile liquid paraffin,
liquid petroleum jelly,
polyolefins and in particular polydecenes,
isoparaffins such as isohexadecane or isododecane and hydrogenated polyisobutylenes such as Parleam® oil sold by the company NOF Corporation (INCI name: Hydrogenated polyisobutene).

Among the mineral oils mentioned above, the following are preferably used:

mixtures of hydrocarbon-based oils derived from petroleum,
volatile or non-volatile liquid paraffin, and
liquid petroleum jelly, and
polyolefins and in particular polydecenes.

The term "polydecenes" is intended to mean any compound of formula $C_{10n}H_{(20n)+2}$ in which n ranges from 3 to 9, corresponding to the name "polydecene" in the CTFA dictionary, 7th edition, 1997, of the Cosmetic, Toiletry and Fragrance Association, USA, and also to the same INCI name in the USA and in Europe. These are poly-1-decene hydrogenation products. Among these compounds, those for which, in the formula, n ranges from 3 to 7 are more particularly chosen according to the invention.

Examples that may be mentioned include preferably the product sold under the name Silkflo® 366 NF Polydecene by the company Amoco Chemical, and those sold under the names Nexbase® 2002 FG, 2004 FG, 2006 FG and 2008 FG by the company Fortum.

The preferred mineral oil is liquid petroleum jelly.

The mineral oil(s) may be present in the composition in a content preferably ranging from 0.1% to 10% by weight and better still from 0.5% to 7% by weight, and more particularly from 1% to 5% by weight of the total weight of the final composition.

The composition according to the invention also comprises one or more esters of fatty alcohol and/or of fatty acid and preferably of fatty acid and of fatty alcohol, and more particularly of saturated fatty acid and of saturated fatty monoalcohol.

The term "fatty alcohol" or "fatty acid" means compounds comprising at least 10 carbon atoms and preferably from 10 to 50 carbon atoms.

The esters of fatty alcohol and/or of fatty acid may be liquid or solid at 25° C. and at atmospheric pressure ($10^5$ Pa).

By way of liquid fatty esters, mention may be made of isopropyl myristate and isopropyl palmitate.

Preferably, the fatty esters of the invention are solid at 25° C. and at atmospheric pressure ($10^5$ Pa). The fatty esters used in the composition of the invention are preferably saturated fatty acid esters, i.e. esters of saturated carboxylic acids comprising at least 10 carbon atoms, and of saturated fatty monoalcohols comprising at least 10 carbon atoms. The saturated acids or monoalcohols may be linear or branched. The saturated carboxylic acids preferably comprise from 10 to 30 carbon atoms and more particularly from 12 to 24 carbon atoms. They may optionally be hydroxylated. The saturated fatty monoalcohols preferably comprise from 10 to 30 carbon atoms and more particularly from 12 to 24 carbon atoms.

Preferably, the esters of fatty alcohol and/or of fatty acid are chosen from myristyl myristate, cetyl myristate, stearyl myristate, myristyl palmitate, cetyl palmitate, stearyl palmitate, myristyl stearate, cetyl stearate, stearyl stearate and behenyl behenate, and mixtures thereof.

The ester(s) of fatty alcohol and/or of fatty acid may be present in the composition in a content ranging from 1% to 20% by weight, preferably from 2% to 15% by weight and more preferably from 4% to 10% by weight relative to the total weight of the composition.

The cosmetic composition according to the invention also comprises one or more surfactants which may be chosen from anionic, cationic, nonionic, amphoteric or zwitterionic surfactants and mixtures thereof.

Preferably, the surfactant(s) are chosen from nonionic surfactants.

The nonionic surfactants which may be used in the compositions of the present invention are compounds well known per se (see especially in this respect "Handbook of Surfactants" by M. R. Porter, published by Blackie & Son (Glasgow and London), 1991, pp. 116-178). They are chosen in particular from polyethoxylated, polypropoxylated or polyglycerolated fatty alcohols, polyethoxylated, polypropoxylated or polyglycerolated alpha-diols, and polyethoxylated, polypropoxylated or polyglycerolated ($C_1$-$C_{20}$) alkylphenols, the fatty chain comprising, for example, from 8 to 18 carbon atoms, it being possible for the number of ethylene oxide or propylene oxide groups to range especially from 1 to 150 and for the number of glycerol groups to range especially from 1 to 30.

Mention may also be made of condensates of ethylene oxide and of propylene oxide with fatty alcohols; polyethoxylated fatty amides preferably having from 1 to 100 ethylene oxide units, polyglycerolated fatty amides comprising on average from 1 to 5 glycerol groups and in particular from 1.5 to 4, ethoxylated esters of fatty acids and of sorbitan having from 1 to 50 ethylene oxide units, sucrose fatty acid esters, esters of fatty acids and of polyethylene glycol, alkylpolyglycosides, polyethoxylated vegetable oils preferably having from 1 to 100 ethylene oxide units, N—($C_6$-$C_{24}$ alkyl)glucamine derivatives or amine oxides, such as ($C_{10}$-$C_{14}$ alkyl)amine oxides or N—($C_{10}$-$C_{14}$ acyl) aminopropylmorpholine oxides.

The alkylpolyglucosides may be chosen, for example, from decylglucoside (alkyl-$C_9$/$C_{11}$-polyglucoside (1.4)), for instance the product sold under the name Mydol 10® by the company Kao Chemicals or the product sold under the name Plantacare 2000 UP® by the company Henkel and the product sold under the name Oramix NS 10® by the company SEPPIC; caprylyl/capryl glucoside, for instance the product sold under the name Plantacare KE 3711® by the company Cognis or Oramix CG 110® by the company SEPPIC; laurylglucoside, for instance the product sold under the name Plantacare 1200 UP® by the company Henkel or Plantaren 1200 N® by the company Henkel; cocoglucoside, for instance the product sold under the name Plantacare 818 UP® by the company Henkel; caprylylglucoside, for instance the product sold under the name Plantacare 810 UP® by the company Cognis; and mixtures thereof.

Preferably, the surfactants are chosen from oxyethylenated fatty alcohols.

The surfactant(s) may be present in a content ranging from 0.1% to 30% by weight, preferably in a content ranging from 0.5% to 15% by weight relative to the total weight of the composition.

According to one embodiment, the composition may comprise one or more oxyethylenated fatty alcohols having from 1 to 5 ethylene oxide unit(s).

Within the context of the present invention, the term "oxyethylenated fatty alcohol" is intended to mean an oxyethylenated alcohol having a hydrocarbon-based chain containing at least 6 carbon atoms.

The term "oxyethylenated fatty alcohol according to the invention" is intended to mean any fatty alcohol having the following structure:

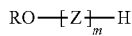

in which:

R denotes a linear or branched, saturated or unsaturated radical comprising from 6 to 40 carbon atoms, in particular from 8 to 30, preferably from 10 to 20, and Z represents an oxyethylenated radical having the following formula:

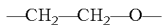

m represents the number of ethylene oxide units ranging from 1 to 5.

Liquid oxyethylenated fatty alcohols which are particularly preferred according to the invention are saturated or unsaturated, linear fatty alcohols comprising from 10 to 20 carbon atoms, especially 16 carbon atoms, and from 2 to 5 ethylene oxide units, in particular two ethylene oxide units.

As compounds of oxyethylenated fatty alcohol type, mention may especially be made of the following products on the market:

Brij S2-SO-(SG) (Croda) [stearyl alcohol 2 EO];
Mergital LM2 (Cognis) [lauryl alcohol 2 EO];
Empilan KA 2.5/90FL (Albright & Wilson) and Mergital BL309 (Cognis) [decyl alcohol 3 EO];
Empilan KA 5/90 FL (Albright & Wilson) and Mergital BL589 (Cognis) [decyl alcohol 5 EO];
Emulgin 05 (Cognis) [oleocetyl alcohol 5 EO].

Preferably, the oxyethylenated fatty alcohol present in the cosmetic composition according to the invention is stearyl alcohol comprising two ethylene oxide units.

When it comprises them, the composition comprises one or more oxyethylenated fatty alcohols having from 1 to 5 ethylene oxide unit(s) in an amount ranging from 0.1% to 10%, preferably from 0.5% to 8% and better still from 2% to 6% by weight relative to the total weight of the composition.

According to one embodiment, the cosmetic composition according to the invention may comprise one or more oxyethylenated nonionic surfactants with unsaturated fatty chain(s) having at least 10 ethylene oxide units. As examples of oxyethylenated nonionic surfactants with unsaturated fatty chain(s), mention may be made of:

oxyethylenated ($C_8$-$C_{24}$)alkylphenols,
unsaturated, linear or branched, oxyethylenated $C_8$-$C_{30}$ and preferably $C_{12}$-$C_{22}$ fatty alcohols,
unsaturated, linear or branched, oxyethylenated $C_8$-$C_{30}$ amides,
polyoxyethylenated esters of unsaturated, linear or branched, $C_8$-$C_{30}$ acids and of sorbitol,
unsaturated oxyethylenated vegetable oils,
and mixtures thereof.

Preferably, the oxyethylenated nonionic surfactants with unsaturated fatty chain(s) are chosen from unsaturated oxyethylenated fatty alcohols.

Within the context of the present invention, the term "unsaturated fatty alcohols" is intended to mean an alcohol comprising at least six carbon atoms and at least one unsaturation within its structure.

In particular, the oxyethylenated nonionic surfactants with unsaturated fatty chain(s) are chosen from unsaturated oxyethylenated fatty alcohols with an unsaturated, linear or branched $C_8$-$C_{30}$ and in particular $C_{10}$-$C_{22}$ fatty chain of the fatty alcohol, and having a number of ethylene oxide units ranging from 10 to 150, such as, for example, the products of addition of ethylene oxide with oleyl alcohol, comprising from 10 to 150 ethylene oxide units (for example CTFA names Oleth-10, Oleth-11, Oleth-12, Oleth-15, Oleth-16, Oleth-20, Oleth-23, Oleth-24, Oleth-25, Oleth-30, Oleth-35, Oleth-40, Oleth-44, Oleth-50, Oleth-82, Oleth-106), the products of addition of ethylene oxide with undecylenyl alcohol comprising from 10 to 50 ethylene oxide units (for example Undeceth-11), and mixtures thereof.

Preferably, the oxyethylenated nonionic surfactants with unsaturated fatty chain(s) of the invention have a number of ethylene oxide units ranging from 10 to 50.

Even more preferably, the oxyethylenated nonionic surfactants with unsaturated fatty chain(s) are chosen from oleyl alcohols having a number of ethylene oxide units ranging from 10 to 50.

When it comprises them, the composition comprises one or more oxyethylenated nonionic surfactants with unsaturated fatty chain(s) having at least 10 ethylene oxide units in an amount ranging from 0.5% to 25% by weight, better still from 1% to 20% by weight and even better still from 2% to 10% by weight relative to the total weight of the composition.

The composition according to the invention also comprises one or more fixing polymers.

Within the context of the invention, the term "fixing polymer" is intended to mean any polymer that is capable, by application to the hair, of giving a shape to the head of hair or of allowing form retention of the hair in an already acquired shape.

The fixing polymer(s) used are chosen from ionic, especially anionic, cationic or amphoteric, and nonionic fixing polymers, and mixtures thereof.

Anionic polymers that may be mentioned include polymers containing groups derived from carboxylic, sulfonic or phosphoric acids, and having a number-average molecular weight of between 500 and 5 000 000.

The carboxylic groups are provided by unsaturated monocarboxylic or dicarboxylic acid monomers, such as those corresponding to the formula:

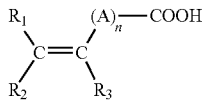

(I)

in which n is an integer from 0 to 10, A denotes a methylene group which is optionally connected to the carbon atom of the unsaturated group or to the neighbouring methylene group when n is greater than 1, via a heteroatom such as oxygen or sulfur, $R_1$ denotes a hydrogen atom or a phenyl or benzyl group, $R_2$ denotes a hydrogen atom, an alkyl group containing from 1 to 4 carbon atoms, or a carboxyl group, $R_3$ denotes a hydrogen atom, an alkyl group containing from 1 to 4 carbon atoms, or a —$CH_2$—COOH, phenyl or benzyl group.

In formula (I) above, the alkyl group containing from 1 to 4 carbon atoms may in particular denote methyl and ethyl groups.

The anionic fixing polymers containing carboxylic or sulfonic groups that are preferred are:

A) Copolymers of acrylic or methacrylic acid or salts thereof and of acrylamide.

B) Copolymers of acrylic or methacrylic acids with a monoethylenic monomer such as ethylene, styrene, vinyl esters, optionally hydroxylated acrylic or methacrylic acid esters, which are optionally grafted on a polyalkylene glycol such as polyethylene glycol, and are optionally crosslinked. Such polymers are described in particular in French patent 1 222 944 and German patent application No. 2 330 956, the copolymers of this type comprising an optionally N-alkylated and/or hydroxyalkylated acrylamide unit in their chain as described especially in Luxembourg patent applications 75370 and 75371. Mention may also be made of copolymers of acrylic acid and of a $C_1$-$C_4$ alkyl methacrylate, methacrylic acid/acrylic acid/ethyl acrylate/methyl methacrylate copolymers, in particular Amerhold DR 25 sold by the company Amerchol, methacrylic acid/ethyl acrylate copolymers, especially as an aqueous dispersion, such as Luviflex Soft and Luvimer MAE sold by the company BASF, and copolymers based on hydroxy esters such as Acudyne 180 from the company Rohm and Haas.

As another anionic fixing polymer from this class, mention may also be made of the branched anionic butyl acrylate/acrylic acid/methacrylic acid block polymer sold under the name Fixate G-100 L by the company Lubrizol (INCI name AMP-Acrylates/Allyl Methacrylate Copolymer).

C) Copolymers derived from crotonic acid, such as those comprising, in their chain, vinyl propionate or acetate units, and optionally other monomers such as allyl or methallyl esters, vinyl ether or vinyl ester of a linear or branched, saturated carboxylic acid with a long hydrocarbon-based chain, such as those comprising at least 5 carbon atoms, it being possible for these polymers optionally to be grafted and crosslinked, or else a vinyl, allyl or methallyl ester of an α- or β-cyclic carboxylic acid. Such polymers are described, inter alia, in French patents Nos. 1 222 944, 1 580 545, 2 265 782, 2 265 781, 1 564 110 and 2 439 798. Commercial products that fall within this category are the resins 28-29-30, 26-13-14 and 28-13-10 sold by the company National Starch.

Mention may also be made, as copolymer derived from crotonic acid, of crotonic acid/vinyl acetate/vinyl tert-butylbenzoate terpolymers, and in particular Mexomere PW supplied by the company Chimex.

D) Polymers derived from maleic, fumaric and/or itaconic acids or anhydrides with vinyl esters, vinyl ethers, vinyl halides, phenylvinyl derivatives, acrylic acid and its esters; these polymers may be esterified. Such polymers are described in particular in U.S. Pat. Nos. 2,047,398, 2,723, 248 and 2,102,113 and GB patent 839 805, and especially those sold under the names Gantrez® AN or ES by the company ISP.

Polymers also falling into this category are the copolymers of maleic, citraconic and/or itaconic anhydrides and of an allyl or methallyl ester optionally comprising an acrylamide or methacrylamide group, an α-olefin, acrylic or methacrylic esters, acrylic or methacrylic acids or vinylpyrrolidone in their chain, the anhydride functions being monoesterified or monoamidated. These polymers are described, for example, in French patents 2 350 384 and 2 357 241 by the applicant.

E) Polyacrylamides comprising carboxylate groups.

F) Polymers comprising sulfonic groups. These polymers may be polymers comprising vinylsulfonic, styrenesulfonic, naphthalenesulfonic, acrylamidoalkylsulfonic or sulfoisophthalate units.

These polymers may in particular be chosen from:
polyvinylsulfonic acid salts having a molecular weight of between approximately 1000 and 100 000, and also copolymers with an unsaturated comonomer, such as acrylic or methacrylic acids and their esters, and also acrylamide or its derivatives, vinyl ethers and vinylpyrrolidone;
polystyrenesulfonic acid salts, sodium salts, having a molecular weight of approximately 500 000 and of about 100 000. These compounds are described in patent FR 2 198 719;
polyacrylamidesulfonic acid salts such as those mentioned in U.S. Pat. No. 4,128,631.

G) Grafted anionic silicone polymers.

The grafted silicone polymers used are preferably chosen from polymers containing a non-silicone organic backbone grafted with monomers containing a polysiloxane, polymers containing a polysiloxane backbone grafted with non-silicone organic monomers, and mixtures thereof.

H) Anionic polyurethanes, possibly comprising silicone grafts and silicones containing hydrocarbon-based grafts.

By way of examples of fixing polyurethanes, mention may be made, in particular, of the dimethylolpropionic acid/isophorone diisocyanate/neopentyl glycol/polyesterdiol copolymer (also known under the name polyurethane-1, INCI nomenclature) sold under the brand name Luviset® PUR by the company BASF, and the dimethylolpropionic acid/isophorone diisocyanate/neopentyl glycol/polyesterdiol/silicone diamine copolymer (also known under the name polyurethane-6, INCI nomenclature) sold under the brand name Luviset® Si PUR A by the company BASF.

Another anionic polyurethane that may also be used is Avalure UR 450.

It is also possible to use polymers containing sulfoisophthalate groups, such as the polymers AQ55 and AQ48 sold by the company Eastman.

According to the invention, the anionic polymers are preferably chosen from acrylic acid copolymers such as the acrylic acid/ethyl acrylate/N-tert-butylacrylamide terpolymer sold under the name Ultrahold Strong® by the company BASF, and methacrylic acid/ethyl acrylate copolymers, especially in aqueous dispersion, such as Luviflex Soft and Luvimer MAE sold by the company BASF. Copolymers derived from crotonic acid such as vinyl acetate/vinyl tert-butylbenzoate/crotonic acid terpolymers and crotonic acid/vinyl acetate/vinyl neododecanoate terpolymers, which are sold under the name Resin 28-29-30 by the company National Starch, polymers derived from maleic, fumaric and/or itaconic acids or anhydrides with vinyl esters, vinyl ethers, vinyl halides, phenylvinyl derivatives, acrylic acid and its esters, such as the monoesterified maleic anhydride/methyl vinyl ether copolymer sold under the name Gantrez® ES 425 by the company ISP, Luviset SI PUR, Mexomere PW, elastomeric or non-elastomeric anionic polyurethanes, and polymers containing sulfoisophthalate groups.

The cationic fixing polymers that may be used according to the present invention are preferably chosen from polymers comprising primary, secondary, tertiary and/or quaternary amine groups forming part of the polymer chain or directly attached thereto, and having a molecular weight of between 500 and approximately 5 000 000 and preferably between 1000 and 3 000 000.

Mention may more particularly be made, among these polymers, of the following cationic polymers:

(1) Homopolymers or copolymers derived from acrylic or methacrylic esters or amides and comprising at least one of the units of following formulae:

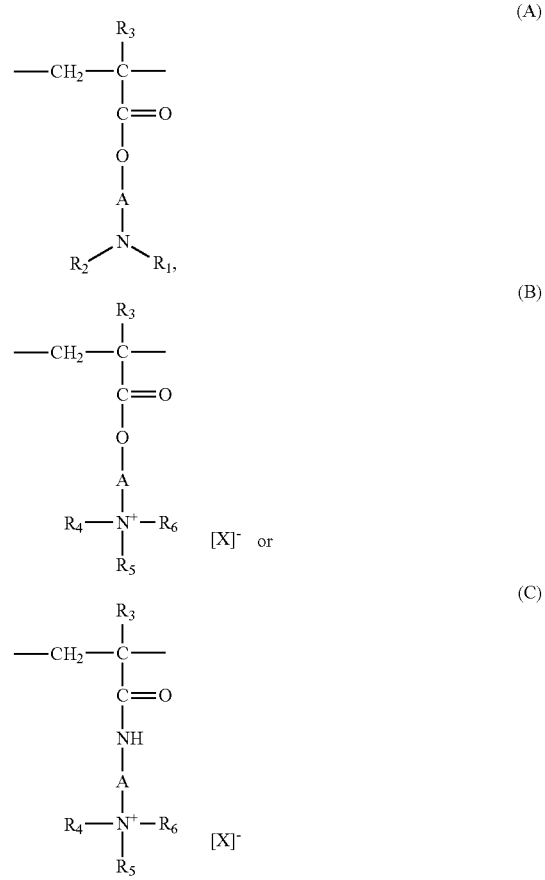

in which:
R$_3$ denotes a hydrogen atom or a CH$_3$ group;
A is a linear or branched alkyl group comprising from 1 to 6 carbon atoms or a hydroxyalkyl group comprising from 1 to 4 carbon atoms;
R$_4$, R$_5$ and R$_6$, which may be identical or different, represent an alkyl group having from 1 to 18 carbon atoms, or a benzyl group;
R$_1$ and R$_2$, which may be identical or different, each represent a hydrogen atom or an alkyl group having from 1 to 6 carbon atoms;
X denotes a methosulfate anion or a halide, such as chloride or bromide.

The copolymers of class (1) further contain one or more units deriving from comonomers which may be chosen from the class of acrylamides, methacrylamides, diacetone acrylamides, acrylamides and methacrylamides substituted on the nitrogen by C$_1$-C$_4$ alkyl groups, groups derived from acrylic or methacrylic acids or esters thereof, vinyllactams such as vinylpyrrolidone or vinylcaprolactam, and vinyl esters.

Thus, among these copolymers of class (1), mention may be made of:
copolymers of acrylamide and of dimethylaminoethyl methacrylate which is quaternized with dimethyl sulfate or with a dimethyl halide, such as that sold under the name Hercofloc® by the company Hercules,
copolymers of acrylamide and of methacryloyloxyethyltrimethylammonium chloride, described for example in patent application EP-A-080976 and sold under the name Bina Quat P 100 by the company Ciba Geigy, the copolymer of acrylamide and of methacryloyloxyethyltrimethylammonium methosulfate, such as that sold under the name Reten by the company Hercules, quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in French patents 2 077 143 and 2 393 573, polymers comprising a fatty chain and comprising a vinylpyrrolidone unit, such as the products sold under the names Styleze W20 and Styleze W10 by the company ISP, dimethylaminoethyl methacrylate/vinylcaprolactam/vinylpyrrolidone terpolymers, such as the product sold under the name Gaffix VC 713 by the company ISP, and quaternized vinylpyrrolidone/dimethylaminopropylmethacrylamide copolymers, such as the products sold under the name Gafquat® HS 100 by the company ISP.

(2) Cationic guar gums, preferably containing quaternary ammonium, such as those described in U.S. Pat. Nos. 3,589,578 and 4,031,307, such as guar gums containing trialkylammonium cationic groups. Such products are sold in particular under the trade names Jaguar C13 S, Jaguar C 15 and Jaguar C 17 by Meyhall.

(3) Quaternary copolymers of vinylpyrrolidone and of vinylimidazole.

(4) Chitosans or salts thereof; the salts which can be used are in particular the acetate, lactate, glutamate, gluconate or pyrrolidonecarboxylate of chitosan.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

(5) Cationic cellulose derivatives, such as copolymers of cellulose or of cellulose derivatives grafted with a water-soluble monomer comprising a quaternary ammonium and described in particular in U.S. Pat. No. 4,131,576, such as hydroxyalkylcelluloses, for instance hydroxymethyl-, hydroxyethyl- or hydroxypropylcelluloses, grafted in particular with a methacryloyloxyethyltrimethylammonium, methacrylamidopropyltrimethylammonium or dimethyldiallylammonium salt.

The commercial products corresponding to this definition are more particularly the products sold under the name Celquat L 200 and Celquat H 100 by the company National Starch.

The amphoteric fixing polymers that can be used in accordance with the invention can be chosen from polymers comprising units B and C distributed randomly in the polymer chain, in which B denotes a unit deriving from a monomer comprising at least one basic nitrogen atom and C denotes a unit deriving from an acid monomer comprising one or more carboxylic or sulfonic groups, or alternatively B and C can denote groups deriving from carboxybetaine or sulfobetaine zwitterionic monomers; B and C can also denote a cationic polymer chain comprising primary, secondary, tertiary or quaternary amine groups, in which at least one of the amine groups bears a carboxylic or sulfonic group connected via a hydrocarbon-based group, or alternatively B and C form part of a chain of a polymer containing an ethylenedicarboxylic unit in which one of the carboxylic groups has been made to react with a polyamine comprising one or more primary or secondary amine groups.

The amphoteric polymers corresponding to the definition given above that are more particularly preferred are chosen from the following polymers:

1) Polymers resulting from the copolymerization of a monomer derived from a vinyl compound bearing a carboxylic group, such as, more particularly, acrylic acid, methacrylic acid, maleic acid or α-chloroacrylic acid, and of a basic monomer derived from a substituted vinyl compound containing at least one basic atom, such as, more particularly, dialkylaminoalkyl methacrylate and acrylate, and dialkylaminoalkylmethacrylamide and -acrylamide. Such compounds are described in U.S. Pat. No. 3,836,537.

The vinyl compound may also be a dialkyldiallylammonium salt such as diethyldiallylammonium chloride.

2) Polymers containing units deriving:

a) from at least one monomer chosen from acrylamides or methacrylamides substituted on the nitrogen with an alkyl group, b) from at least one acidic comonomer comprising one or more reactive carboxylic groups, and c) from at least one basic comonomer, such as esters with primary, secondary, tertiary and quaternary amine substituents of acrylic and methacrylic acids, and the product of quaternization of dimethylaminoethyl methacrylate with dimethyl or diethyl sulfate.

The N-substituted acrylamides or methacrylamides which are more particularly preferred according to the invention are groups in which the alkyl groups contain from 2 to 12 carbon atoms, and more particularly N-ethylacrylamide, N-tert-butylacrylamide, N-tert-octylacrylamide, N-octylacrylamide, N-decylacrylamide, N-dodecylacrylamide, and also the corresponding methacrylamides.

The acidic comonomers are chosen more particularly from acrylic, methacrylic, crotonic, itaconic, maleic and fumaric acids and also the alkyl monoesters having 1 to 4 carbon atoms of maleic or fumaric acids or anhydrides. The preferred basic comonomers are aminoethyl, butylaminoethyl, N,N'-dimethylaminoethyl and N-tert-butylaminoethyl methacrylates. The copolymers of which the CTFA (4th edition, 1991) name is octylacrylamide/acrylates/butylaminoethyl methacrylate copolymer, such as the products sold under the name Amphomer® or Lovocryl® 47 by the company National Starch, are particularly used.

3) Alkylated and crosslinked polyaminoamides deriving wholly or partly from polyaminoamides of general formula:

(II)

in which $R_4$ represents a divalent group derived from a saturated dicarboxylic acid, from a mono- or dicarboxylic aliphatic acid with an ethylenic double bond, from an ester of an alcohol having 1 to 6 carbon atoms with these acids, or from a group deriving from the addition of any one of said acids with a bis-primary amine or bis-secondary-derived amine, and Z denotes a group of a bis-primary or mono- or bis-secondary polyalkylene-polyamine, and preferably represents:

a) in proportions of from 60 mol % to 100 mol %, the group

(III)

where x=2 and p=2 or 3, or else x=3 and p=2, this group deriving from diethylenetriamine, triethylenetetramine or dipropylenetriamine;

b) in proportions of from 0 to 40 mol %, the group (III) above, in which x=2 and p=1, which derives from ethylenediamine, or the group deriving from piperazine

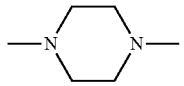

c) in proportions of from 0 to 20 mol %, the —NH(CH$_2$)$_6$—NH— group deriving from hexamethylenediamine, these polyaminoamines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyaminoamide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid; 2,4,4-trimethyladipic acid and terephthalic acid, and acids having an ethylenic double bond, such as, for example, acrylic, methacrylic and itaconic acids. The alkane sultones used in the alkylation are preferably propane sultone or butane sultone; the salts of the alkylating agents are preferably the sodium or potassium salts.

4) Polymers containing zwitterionic units of formula:

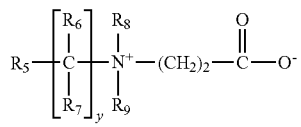

in which R$_5$ denotes a polymerizable unsaturated group, such as an acrylate, methacrylate, acrylamide or methacrylamide group, y and z each represent an integer from 1 to 3, R$_6$ and R$_7$ represent a hydrogen atom or a methyl, ethyl or propyl group, R$_8$ and R$_9$ represent a hydrogen atom or an alkyl group such that the sum of the carbon atoms in R$_{10}$ and R$_{11}$ does not exceed 10.

The polymers comprising such units can also comprise units derived from non-zwitterionic monomers such as dimethyl- or diethylaminoethyl acrylate or methacrylate or alkyl acrylates or methacrylates, acrylamides or methacrylamides or vinyl acetate.

5) Polymers derived from chitosan comprising monomer units corresponding to the following formulae:

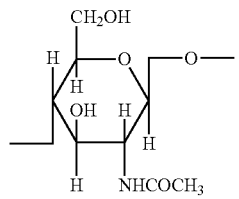

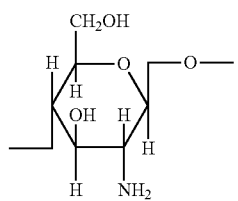

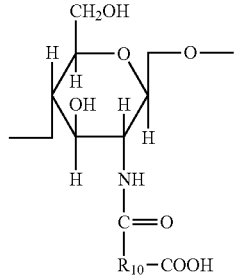

the unit (V) being present in proportions of between 0 and 30%, the unit (VI) in proportions of between 5% and 50% and the unit (VII) in proportions of between 30% and 90%, it being understood that, in this unit F, R$_{10}$ represents a group of formula:

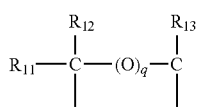

in which, if q=0, R$_{11}$, R$_{12}$ and R$_{13}$, which may be identical or different, each represent a hydrogen atom, a methyl, hydroxyl, acetoxy or amino residue, a monoalkylamine residue or a dialkylamine residue that are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the groups R$_{17}$, R$_{18}$ and R$_{19}$ being, in this case, a hydrogen atom;

or, if q=1, R$_{11}$, R$_{12}$ and R$_{13}$ each represent a hydrogen atom, and also the salts formed by these compounds with bases or acids.

6) Polymers derived from the N-carboxyalkylation of chitosan.

7) Polymers of units corresponding to general formula (IX), described, for example, in French patent 1 400 366:

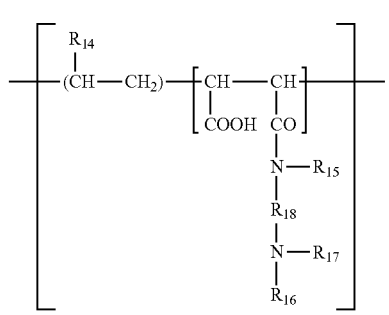

in which $R_{14}$ represents a hydrogen atom or a $CH_3O$, $CH_3CH_2O$, or phenyl group, $R_{15}$ denotes hydrogen or a $C_1$-$C_4$ alkyl group such as methyl and ethyl, $R_{16}$ denotes hydrogen or a $C_1$-$C_4$ alkyl group such as methyl and ethyl, $R_{17}$ denotes a $C_1$-$C_4$ alkyl group such as methyl and ethyl or a group corresponding to the formula: —$R_{18}$—$N(R_{16})_2$, with $R_{18}$ representing a —$CH_2$—$CH_2$—, —$CH_2$—$CH_2$—$CH_2$—, or —$CH_2$—$CH(CH_3)$— group and $R_{16}$ having the meanings given above, and also the higher homologs of these groups, containing up to 6 carbon atoms.

8) Amphoteric polymers of the type -D-X-D-X—, chosen from:

a) polymers obtained by the action of chloroacetic acid or sodium chloroacetate on compounds comprising at least one unit of formula:

-D-X-D-X-D-              (X)

where D denotes a group

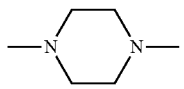

and X denotes the symbol E or E', where E or E', which may be identical or different, denote a divalent group that is an alkylene group with a straight or branched chain containing up to 7 carbon atoms in the main chain, which is unsubstituted or substituted with hydroxyl groups and which can comprise, in addition to oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X—              (XI)

where D denotes a group

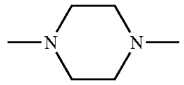

and X denotes the symbol E or E' and at least once E'; E having the meaning given above and E' is a divalent group that is an alkylene group with a straight or branched chain having up to 7 carbon atoms in the main chain, which is unsubstituted or substituted with one or more hydroxyl groups and which contains one or more nitrogen atoms, the nitrogen atom being substituted with an alkyl chain that is optionally interrupted by an oxygen atom and necessarily comprises one or more carboxyl functions or one or more hydroxyl functions, betainized by reaction with chloroacetic acid or sodium chloroacetate.

9) ($C_1$-$C_5$)Alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers may also comprise other vinyl comonomers such as vinylcaprolactam.

According to one preferred embodiment of the invention, the amphoteric fixing polymers that may be used in the aerosol device according to the invention may be chosen from branched block copolymers comprising:

(a) nonionic units derived from at least one monomer chosen from $C_1$-$C_{20}$ alkyl (meth)acrylates, N-mono-($C_2$-$C_{12}$ alkyl)(meth)acrylamides and N,N-di($C_2$-$C_{12}$ alkyl)(meth)acrylamides, (b) anionic units derived from at least one monomer chosen from acrylic acid and methacrylic acid, and (c) polyfunctional units derived from at least one monomer containing at least two polymerizable unsaturated functional groups, and preferably having a structure constituted of hydrophobic blocks onto which are fixed, via polyfunctional units (c), several blocks which are more hydrophilic.

Preferably, the amphoteric polymers have at least two glass transition temperatures (Tg), at least one of which is greater than 20° C. and the other of which is less than 20° C.

The preferred amphoteric polymers are polymers comprising units deriving:

a) from at least one monomer chosen from acrylamides or methacrylamides substituted on the nitrogen with an alkyl group, b) from at least one acidic comonomer comprising one or more reactive carboxylic groups, and c) from at least one basic comonomer such as acrylic and methacrylic acid esters containing primary, secondary, tertiary and quaternary amine substituents, and the product of quaternization of dimethylaminoethyl methacrylate with dimethyl or diethyl sulfate.

Mention may be made in particular of the polymers sold under the name Amphomer by the company National Starch.

The nonionic fixing polymers that may be used according to the present invention are chosen, for example, from:

polyalkyloxazolines,
vinyl acetate homopolymers,
vinyl acetate copolymers, for instance copolymers of vinyl acetate and of acrylic ester, copolymers of vinyl acetate and of ethylene, or copolymers of vinyl acetate and of maleic ester, for example dibutyl maleate,
acrylic ester homopolymers and copolymers, for instance copolymers of alkyl acrylates and of alkyl methacrylates, such as the products provided by the company Rohm & Haas under the names Primal® AC-261 K and Eudragit® NE 30 D, by the company BASF under the name 8845, or by the company Hoechst under the name Appretan® N9212,
copolymers of acrylonitrile and of a nonionic monomer chosen, for example, from butadiene and alkyl (meth)acrylates, such as the products provided under the name CJ 0601 B by the company Rohm & Haas,
styrene homopolymers,
styrene copolymers, for instance copolymers of styrene and of alkyl(meth)acrylate, such as the products Mowilith® LDM 6911, Mowilith® DM 611 and Mowilith® LDM 6070 provided by the company Hoechst, the products Rhodopas® SD 215 and Rhodopas® DS 910 provided by the company Rhône-Poulenc, copolymers of styrene, of alkyl methacrylate and of alkyl acrylate, copolymers of styrene and of butadiene, or copolymers of styrene, of butadiene and of vinylpyridine,
polyamides,
vinyllactam homopolymers such as vinylpyrrolidone homopolymers and such as the polyvinylcaprolactam sold under the name Luviskol® Plus by the company BASF, vinyllactam copolymers, such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA® S630L by the company ISP, Luviskol® VA 73, VA 64, VA 55, VA 37 and VA 28 by the company BASF and poly(vinylpyrrolidone/vinyl acetate/vinyl propionate) terpolymers, for instance the product sold under the name Luviskol® VAP 343 by the company BASF, and poly(vinyl alcohols).

The alkyl groups of the nonionic polymers mentioned above preferably have from 1 to 6 carbon atoms.

Preferably, the fixing polymer is a nonionic or cationic fixing polymer.

Even more preferably, the fixing polymer is a nonionic fixing polymer.

The fixing polymers may be present in the composition in an amount ranging from 0.5% to 25%, preferably from 0.7% to 20% and more preferably from 1% to 17 by weight relative to the total weight of the composition.

Preferably, the composition comprises water, preferably in a content of greater than or equal to 5% by weight relative to the total weight of the composition. Preferably, the water content ranges from 5% to 98%, preferably from 10% to 95%, better still from 20% to 80% and even better still from 30% to 70% by weight relative to the total weight of the composition.

The composition may also comprise one or more water-soluble liquid organic solvents, preferably chosen from monoalcohols such as ethanol or isopropanol, polyols such as propylene glycol, butylene glycol or glycerol, polyol ethers, and mixtures thereof.

The composition according to the invention may comprise a propellant. For example, mention may be made of liquefied gases such as dimethyl ether, 1,1-difluoroethane, or $C_3$-$C_5$ alkanes, for instance propane, isopropane, n-butane, isobutane or pentane, or compressed gases such as air, nitrogen or carbon dioxide, and mixtures thereof.

Preferably, use will be made of $C_3$-$C_5$ alkanes and in particular propane, n-butane and isobutane and mixtures thereof.

When it comprises them, the composition comprises one or more propellant(s) in an amount ranging from 1% to 60% by weight, even better still from 2% to 50% by weight and even more preferably from 4% to 40% by weight relative to the total weight of the composition.

The composition according to the invention may also contain one or more additive(s) other that the compounds of the invention, chosen from non-silicone-based conditioning agents, silicones, vitamins and provitamins including panthenol, sunscreens, pearlizing and opacifying agents, dyes, sequestrants, thickeners, plasticizers, solubilizers, acidifying agents, basifying agents, neutralizing agents, antioxidants, antifoams, moisturizing agents, emollients, hydroxy acids, penetrating agents, fragrances, preservatives and fillers and solid particles such as for example colored or colorless organic and inorganic pigments.

These additives may be present in the composition according to the invention in an amount ranging from 0 to 20% by weight relative to the total weight of the composition.

Needless to say, a person skilled in the art will take care to select the optional additional compounds and/or the amount thereof such that the advantageous properties of the compositions used according to the invention are not, or are not substantially, adversely affected by the envisioned addition.

The composition according to the invention may be in the form, inter alia, of liquids that are more or less thickened, gels, serums, creams, pastes, sprays or foams.

In particular, the composition of the invention may be applied using an aerosol device.

Preferably, the composition according to the invention is in the form of gels, creams or pastes, preferably in the form of a cream.

The cosmetic composition according to the invention may be advantageously used for cosmetic hair treatment. In particular, it may be used for hairstyling, for example for shaping and/or form retention of the hairstyle.

The present invention also relates to a process for the cosmetic treatment of the hair, for example a process for shaping and/or form retention of the hairstyle, which consists in applying, to the hair, an effective amount of a composition according to the invention as described earlier, and then in carrying out an optional rinsing after an optional leave-in time.

Preferably, the composition according to the invention is not rinsed off.

The process of the invention may be carried out at ambient temperature (25° C.) or under heat, at a temperature ranging from 40 to 230° C. using any heating device: hood, hairdryer, tongs.

The invention is illustrated in more detail in the example that follows, which is given as a non-limiting illustration of the invention.

EXAMPLE

Two styling creams were produced using the ingredients indicated in the table below as percentage by weight of product in unmodified form:

| Chemical name | A | B |
|---|---|---|
| Liquid petroleum jelly [1] | 2 | 2.5 |
| Hydrocarbon (C20/C60) mineral wax [2] | 15 | 13.5 |
| Vinylpyrrolidone/dimethylaminoethyl methacrylate copolymer at 20% in water [3] | 6 | — |
| Vinylpyrrolidone/vinyl acetate copolymer (60/40) in aqueous solution (50%) | 6 | 8 |
| Oxyethylenated stearyl alcohol (2 EO) [4] | 4 | 4 |
| Triethanolamine (99%) | 1.2 | 1.2 |
| Myristyl/cetyl/stearyl myristate/palmitate/stearate mixture [5] | 7 | 7 |
| Ethylenediaminetetraacetic acid, disodium salt, 2 H$_2$O | 0.1 | 0.1 |
| 1,2-Octanediol | 1 | 1 |
| Fatty acids of plant origin (53% stearic acid-palmitic acid-stearic acid) [6] | 3 | 3 |
| Polydimethylsiloxane (viscosity 5 cSt) | 4 | 7.5 |
| Microcrystalline wax (melting point 74-79° C.) [7] | 10 | 8.5 |
| Carboxyvinyl polymer [8] | 0.2 | 0.2 |
| Oleth-30 [9] | 6 | 6 |

-continued

| Chemical name | A | B |
|---|---|---|
| Fragrance | 0.6 | 0.6 |
| Preservative | 1 | 1 |
| Water | qs 100 | qs 100 |

(1) Blandol sold by the company Sonneborn
(2) Ozokerite Wax SP 1020 P sold by the company Strahl & Pitsch
(3) Copolymer 845-O sold by the company Ashland
(4) Brij S2-SO-(SG) sold by the company Croda
(5) Crodamol MS-PA-(MH) sold by the company Croda
(6) Palmera B1802CG sold by the company KLK Oleo
(7) White Microcrystalline Wax SP-18 sold by the company Strahl & Pitsch
(8) Synthalen K sold by the company 3V
(9) Eumulgin O 30 sold by the company Cognis The creams A and B were applied to dry hair.

The creams obtained are easy to take up and to spread out in the hands. They can be easily transferred from the hands to the hair and are easy to spread out on the hair. The creams are not very sticky but enable the hairstyle to be shaped. Moreover, the hairstyle is quickly shaped.

A hairstyle with a natural finish is obtained. The hair does not form clumps.

Good, lasting hold of the hairstyle, which is moreover easy to restyle, is obtained.

The invention claimed is:

1. A cosmetic composition comprising:
    at least one mineral wax, wherein the mineral wax is ozokerite, wherein the mineral wax is present in an amount ranging from 12% to 30% by weight, relative to the total weight of the composition;
    at least one fatty acid present in an amount ranging from 1% to 5% by weight, relative to the total weight of the composition;
    at least one mineral oil;
    at least one surfactant;
    at least one ester of fatty acid and/or of fatty alcohol present in an amount ranging from 4% to 10% by weight, relative to the total weight of the composition;
    at least one fixing polymer; and
    at least one oxyethylenated nonionic surfactant comprising at least one unsaturated fatty chain having at least 10 ethylene oxide units,
    wherein the at least one ester of fatty acid and/or of fatty alcohol is
    a) solid at 25° C. and at atmospheric pressure ($10^5$ Pa), and
    b) chosen from esters of saturated fatty acid and of saturated fatty monoalcohol.

2. The composition according to claim 1, wherein the at least one fatty acid is chosen from stearic acid, palmitic acid, myristic acid, behenic acid, or mixtures thereof.

3. The composition according to claim 1, wherein the at least one mineral oil is chosen from mixtures of hydrocarbon-based oils derived from petroleum, volatile or non-volatile liquid paraffin, liquid petroleum jelly, polyolefins, polydecenes, isoparaffins, isohexadecane, isododecane, hydrogenated polyisobutylenes, or mixtures thereof.

4. The composition according to claim 1, wherein the mineral oil is present in an amount ranging from 0.1% to 10% by weight, relative to the total weight of the composition.

5. The composition according to claim 1, wherein the at least one surfactant is chosen from anionic, cationic, nonionic, amphoteric, or zwitterionic surfactants or mixtures thereof.

6. The composition according to claim 1, wherein the surfactant is present in an amount ranging from 0.1% to 30% by weight, relative to the total weight of the composition.

7. The composition according to claim 1, wherein the at least one ester of fatty acid and/or of fatty alcohol is chosen from myristyl myristate, cetyl myristate, stearyl myristate, myristyl palmitate, cetyl palmitate, stearyl palmitate, myristyl stearate, cetyl stearate, stearyl stearate, behenyl behenate, or mixtures thereof.

8. The composition according to claim 1, wherein the at least one fixing polymer is chosen from nonionic, anionic, cationic, or amphoteric fixing polymers.

9. The composition according to claim 1, wherein the at least one fixing polymer is chosen from nonionic fixing polymers.

10. The composition according to claim 1, wherein the fixing polymer is present in an amount ranging from 0.5% to 25% by weight, relative to the total weight of the composition.

11. The composition according to claim 1, further comprising at least one oxyethylenated fatty alcohol having from 1 to 5 ethylene oxide units.

12. The composition according to claim 1, further comprising water, wherein the water is present in an amount ranging from 5% to 98% by weight, relative to the total weight of the composition.

13. A process for the cosmetic treatment of keratin fibers, comprising applying to the keratin fibers an effective amount of a composition, the composition comprising:
    at least one mineral wax, wherein the mineral wax is ozokerite, wherein the mineral wax is present in an amount ranging from 12% to 30% by weight, relative to the total weight of the composition;
    at least one fatty acid present in an amount ranging from 1% to 5% by weight, relative to the total weight of the composition;
    at least one mineral oil;
    at least one surfactant;
    at least one ester of fatty acid and/or of fatty alcohol present in an amount ranging from 4% to 10% by weight, relative to the total weight of the composition;
    at least one fixing polymer; and
    at least one oxyethylenated nonionic surfactant comprising at least one unsaturated fatty chain having at least 10 ethylene oxide units,
    wherein the at least one ester of fatty acid and/or of fatty alcohol is
    a) solid at 25° C. and at atmospheric pressure ($10^5$ Pa), and
    b) chosen from esters of saturated fatty acid and of saturated fatty monoalcohol.

* * * * *